United States Patent [19]

Kumagai et al.

[11] Patent Number: 5,559,211
[45] Date of Patent: Sep. 24, 1996

[54] **BIOLOGICALLY ACTIVE PRODUCT PRODUCED BY *STREPTOCOCCUS PYOGENES* AND METHOD OF PURIFICATION**

[75] Inventors: Katsuo Kumagai, Sendai; Hidemi Rikiishi, Tagajo; Keiji Tamura; Shunji Sugawara, both of Sendai; Eiji Nemoto, Tokyo; Shigefumi Okamoto, Sendai; Tokio Onta, Tokyo, all of Japan

[73] Assignee: Kabushiki Kaisha Saikin Kagaku Kenkyujo, Miyagi-ken, Japan

[21] Appl. No.: 198,345

[22] Filed: Feb. 18, 1994

[30] Foreign Application Priority Data

Jun. 11, 1993 [JP] Japan ................ 5-140893

[51] Int. Cl.⁶ .................. C07K 14/315; C07K 1/36; C12N 1/20; C12Q 1/02
[52] U.S. Cl. .................. 530/350; 530/416; 530/417; 435/29; 435/253.4; 435/803; 435/885
[58] Field of Search .................. 530/350, 416, 530/417; 435/29, 885, 803, 253.4

[56] References Cited

U.S. PATENT DOCUMENTS

| 4,772,584 | 9/1988 | Clearly et al. ............... 514/2 |
| 4,929,547 | 5/1990 | Kanoaka et al. ............ 435/69.1 |

OTHER PUBLICATIONS

Hoh et al. Infect Immun. 60(8) 3128–3135 1992.
Manjua et al. J. Immunol 124(1) 261–267 1980.
Joklik et al "Zinsser Microbiology" 20th ed. 8–17, 749–782 1992.
Harris et al. "Protein Purification Methods" p. 61–63, 148–160, 180–181, 295–301, 1991.
Hoh et al. "Mechanism of Stimulation of T Cells by *Streptococcus pyogenes*: Isolation of a Major Mitogenic Factor, Cytoplasmic Membrane Associated Protein" Infect Immun. 60(8) 3128–3135 1992.
Manjula et al. "Studies on Group A Streptococcal M–Proteins: Purification of Type 5–M–Protein & Comparison of its Amino Terminal Sequence w/ Two Immunologically Unrelated M Protein Molecules" J. Immunol. 124(1) 261–267 1980.

*Primary Examiner*—Mindy Fleisher
*Assistant Examiner*—Nancy J. Degen
*Attorney, Agent, or Firm*—Sixbey, Friedman, Leedom & Ferguson

[57] ABSTRACT

A biologically active, stable protein with a molecular weight of 20,000 to 30,000 and an isoelectric point of 8.0–10.0 is produced from the culture fluid of *Streptococcus pyogenes* and purified. The purified biologically active protein produces lymphocyte proliferation, provides protection against bacterial and viral infection and restricts minor metastasis.

4 Claims, 1 Drawing Sheet

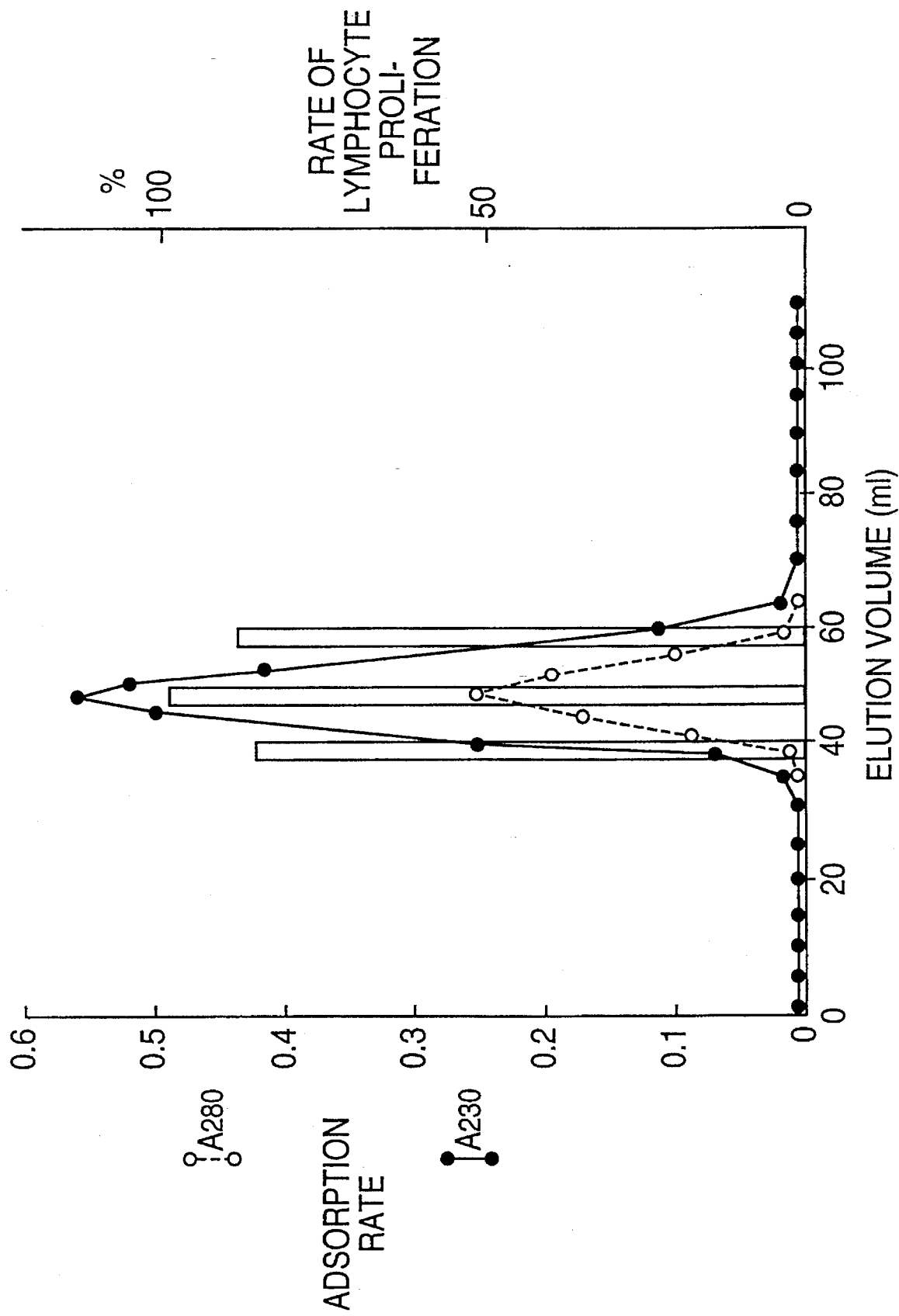

BIOLOGICALLY ACTIVE PRODUCT PRODUCED BY *STREPTOCOCCUS PYOGENES* AND METHOD OF PURIFICATION

TECHNICAL FIELD

The present invention relates generally to biologically active proteins and specifically to a biologically active protein produced by *Streptococcus pyogenes*.

BACKGROUND OF THE INVENTION

The anti-tumor activity of live *Streptococcus pyogenes* bacteria (hereinafter *S. pyogenes*) has been known for many years. However, *S. pyogenes* includes most of the highly pathogenic strains of streptococci and can cause severe systemic and local infections. Consequently, live *S. pyogenes* bacteria have not been used to treat tumors because of their disease-causing potential.

The effective utilization of the anti-tumor activity of the pathogenic *S. pyogenes* is a problem that has not been solved satisfactorily. One approach has been to treat an attenuated strain of live *S. pyogenes* bacteria with a relatively high concentration of penicillin G. The treated *S. pyogenes* bacteria are then freeze-dried to produce the anti-cancer drug picibanil. However, this process requires the use of whole pathogenic bacteria as raw materials. The whole bacteria must be handled and maintained carefully and consistently to provide a stable supply of a usable product. This has proved difficult, and obtaining a consistent supply of a used anti-tumor agent from *S. pyogenes* has not heretofore been achieved.

A need exists, therefore, for a way to utilize the anti-tumor and other biological activity of *S. pyogenes* that does not have the drawbacks which accompany the production of the available anti-cancer product produced by whole *S. pyogenes* bacteria.

SUMMARY OF THE INVENTION

It is a primary object of the present invention to overcome the disadvantages of the prior art and to provide a usable biologically active substance from pathogenic *S. pyogenes*.

It is another object of the present invention to provide a stable and consistent anti-tumor agent from *S. pyogenes*.

It is yet another object of the present invention to provide a method for purifying a biologically active substance from *S. pyogenes*.

The foregoing objects are achieved by providing a purified biologically-active protein isolated from the culture fluid of a culture of *S. pyogenes* which has consistent physicochemical and biological characteristics. This biologically active protein has a molecular weight of about 20,000 to 30,000 and has been demonstrated to activate and proliferate lymphocytes, to provide protection against infection and to display anti-tumor activity.

Other objects and advantages will be apparent from the following description, claims and drawing.

BRIEF DESCRIPTION OF THE DRAWINGS

The sole FIGURE is a graphic representation of the elution curve and biological activity of the purified biologically active protein of the present invention.

DESCRIPTION OF THE PREFERRED EMBODIMENTS

The inventors of the present invention studied the culture fluid of *S. pyogenes* and isolated and purified from the culture fluid a biologically active protein. This protein was demonstrated to produce lymphocyte proliferation, protection against infection and antagonism to cancer.

Any strain of *S. pyogenes* can be used to produce the biologically active protein of the present invention. Particularly preferred strains of *S. pyogenes* include *Streptococcus pyogenes* Su (ATCC 21060), *Streptococcus pyogenes* Sv (ATCC 21059), *Streptococcus pyogenes* T-12 (ATCC 12353) and *Streptococcus pyogenes* C-203 (ATCC 12384).

The biologically active protein of the present invention is produced by incubating the selected strain of *S. pyogenes* in a liquid culture medium. A preferred liquid medium is produced as follows:

| | |
|---|---|
| minced beef | 10 grams |
| tryptophan | 20 grams |
| glucose | 2 grams |
| $NaHCO_3$ | 2 grams |
| NaCl | 2 grams |
| $Na_2HPO_4$ | 0.4 gram |
| distilled water | 1.0 liter |

The pH is adjusted to 7.8, and the mixture autoclaved for 10 minutes at 115° C. The culture medium is then inoculated with the selected strain of *S. pyogenes* and shaken or stirred. The biologically active substance is obtained from the *S. pyogenes* culture by centrifugation of the culture fluid and collection of the supernatant.

The initial purification of the biologically active substance of the present invention from the *S. pyogenes* culture fluid supernatant can be accomplished by conventional purification methods, including, but not limited to, ammonium sulfate precipitation, ion-exchange column chromatography, gel filtration and freeze-drying.

The biologically active substance isolated from *S. pyogenes* has a molecular weight of about 23,000 to 27,000 as determined by SDS sodium dodecyl sulfate polyacrylamide gel electrophoresis and about 20,000 to 30,000 as determined by gel filtration. This biologically active substance has been determined to be a protein with the amino acid composition in Table I.

TABLE I

| Amino Acid | Nanomol % |
|---|---|
| Aspartic acid | 3.2 |
| Threonine | 7.5 |
| Serine | 2.9 |
| Glutamic acid | 19.5 |
| Proline | 1.9 |
| Glycine | 30.0 |
| Alanine | 2.3 |
| Cystine | not determined |
| Valine | 4.7 |
| Methionine | 3.6 |
| Isoleucine | 1.3 |
| Leucine | 11.5 |
| Tyrosine | 0.3 |
| Phenylalanine | 2.0 |
| Lysine | 2.2 |
| Histidine | 5.2 |
| Arginine | 1.9 |

The isoelectric point is 8.0–10.0, as determined by the electrofocusing method available from Pharmacia Fine Chemicals.

The biologically active protein of the present invention is highly stable, and this stability is demonstrated under various conditions, including acid and alkaline treatment, temperature and enzyme treatment as described in Table II.

TABLE II

| Treatment | Conditions | Stability |
|---|---|---|
| Hydrochloric Acid | pH 4.0 for 10 min. | Stable |
| Sodium Hydroxide | pH 9.0 for 10 min. | Stable |
| Heat | 100° C. for 5 min. | Stable |
| Cold | −20 to −80° C. for 6 months | Stable |
| Trypsin | — | Stable |
| Phospholipase $A_2$ | — | Stable |
| Phospholipase C | — | Stable |
| Proteinase K | — | Stable |
| Neuraminidase | — | Stable |
| Galactooxidase | — | Stable |

The biologically active protein of the present invention was compared with existing bacterial products and was found to react differently than the existing products. For example, the pyrogenic exotoxin A of S. pyogenes produces lymphocyte proliferation by a reaction which induces interleukin-2 (IL-2) to stimulate lymphocyte proliferation. The biologically active protein of the present invention produces lymphocyte proliferation without the participation of IL-2. Moreover, the novel protein of the present invention does not react with anti-streptococcal pyrogenic exotoxin A produced from rabbit serum, which further demonstrates that it is an active substance completely distinct from the products known to be produced by S. pyogenes.

The S. pyogenes active substance of the present invention can be used to produce lymphocyte proliferation, to provide protection against bacterial and viral diseases and to antagonize tumors or cancers without the dangers and drawbacks associated with exposing the human or animal patients to the highly pathogenic whole S. pyogenes bacteria as required in the past. The following Examples illustrate the production of the biologically active substance of the present invention and its uses.

Example 1

The active substance is isolated frown S. pyogenes and purified as follows. At 4° C. ammonium sulfate was added to 60% saturation to the culture fluid of a culture of S. pyogenes T12 and allowed to stand for 1 hour. The precipitate was collected by centrifugation at 8,000×G for 30 minutes and dialyzed into 20 mM acetate buffer at pH 5.0. A 30×50 cm column was stuffed with CM-cellulose (Wattsnan) and equilibrated with the acetate buffer. The dialyzed solution was added to the column, followed by 0.1M acetate buffer. The eluted fraction was collected and disposed of. An active fraction was collected by elution with 0.5 M acetate buffer. This active fraction was dialyzed and then freeze-dried.

The freeze-dried active fraction was run through a 2.0×100 cm column filled with Sephacryl S-200 (Pharmacia) and equilibrated with 20 mM Tris-HCl buffer at pH 7.4. A fraction of molecular weight 20,000 to 30,000 was eluted with the same buffer and collected. This collected fraction was then added to a 1.2×100 cm Sephadex G-50 column (Pharmacia) and diluted with the 20 mM Tris-HCl buffer. The first eluted fraction was discarded, and the fraction of molecular weight 20,000 to 30,000 was collected and freeze-dried. This freeze-dried fraction was then run through the same Sephadex G-50 column to purify it. The active substance obtained from the column was observed to be a single band by acrylamide gel electrophoresis. The comparative activity of this substance to proliferate lymphocytes as described below was measured at 600 fold dilution.

Example 2

Mononuclear cells were collected from the peripheral blood cells of a healthy human donor. Mononuclear cells were also collected from spleen cells of C3H/HeN and BALB/c strains of mice. The Ficoll-isopaque method, available from Pharmacia, was used for this process. The lymphocyte proliferation activity of the active substance produced according to Example 1 was measured by the incorporation in the cells of [$^3$H] thymidine.

RPMI 1640 medium containing L-glutamine was used as the culture fluid for the lymphocytes. Autoserum inactivated for 30 minutes at 56° C. was added to the culture medium to a level of 10%. Significant proliferation of the human and mouse lymphocytes was observed from the 5th to the 8th clay after 0.01–10 µg/ml of the active substance of Example 1 was added to the mononuclear cells.

This result occurred without the presence of human interleukin-2, which was previously thought to be necessary. The observed lymphocyte proliferation also indicates that the novel active substance is new and differs from Phytohemagglutinin, which is a T cells growth factor, and from Concanavalin A.

The sole drawing illustrates the elution curve and biological activity of the purified products of the present invention in Sephadex 50 column chromatography. The left vertical axis shows the adsorption rate at A230 nm and at A280 nm, which are represented by the solid and dashed curves, respectively. The right vertical axis shows the rate of lymphocyte proliferation, which is represented by the bars. The rate of lymphocyte proliferation is calculated using 100 for the maximum incorporation of [$^3$H] thyroidinc into the cells when the active substance is added and using 1 when the active substance is not added. The elution volume is shown on the horizontal axis.

Example 3

The effect of the active substance of Example 1 on bacterial infection was determined by measuring the seventh (7th) day survival rate after infection of mice. Four week old male mice of the strain C3H/HeN were injected peritoneally with 100 µg/dose/day of the active substance of Example 1 from the fourth to the first day prior to infection with 3×10$^5$ S. pyogenes C203. A control group was not injected with the active substance prior to infection with S. pyogenes C203. All of the mice in the control group died, while all of the mice injected with the active substance prior to S. pyogenes infection survived. This demonstrates that the active substance isolated from S. pyogenes provides significant protection against infection by S. pyogenes.

The effective infection prevention capability of the active substance of Example 1 against other bacterial infections was further demonstrated by an additional study in which one group of four week old male C3H/HeN mice was injected peritoneally with 100 µg/dose/day of the active substance from the fourth to the first day prior to infection with 3×10$^5$ *Listeria monocytogenes* EGD by intravenous injection. A control group received no injections of active substance prior to infection with the Listeria. The survival rate on the fourteenth day after infection was 71.4% (5 out of 7) for the group receiving the pre-infection injections of active substance and 0% for the control group.

Example 4

The active substance of Example 1 is also effective in preventing viral infections. This was demonstrated by the peritoneal injection of 100 μg/ml of active substance into six week old male C3H/HeN mice prior to infection with 10 PFU of Herpes simplex virus (HSV-1, Miyama strain). One injection of the S. pyogenes active substance was injected on the third, second or first day prior to infection with the Herpes virus. The vital infective agent was also administered at one dose per day for three days. A control group received no injection of active substance prior to infection. The survival rate on the 20th day after infection was measured. None of the control group survived, while all of the mice that had received the pre-infection injections of active substance survived. This demonstrates that the active substance isolated from S. pyogenes has a protective capability against vital infections.

Example 5

The anti-tumor effect of the biologically active substance of Example 1 was demonstrated in mice. 100 μg/dose/day of the S. pyogenes active substance was injected peritoneally into six week old male BALB/c mice on the third, second and first day prior to the intravenous injection of tumor cells. $2 \times 10^6$ cells of an RL♂1 type tumor, which is metasiatic to the liver, were intravenously injected into the group of mice that had received injections of active substance and into a control group that had not received such injections. Metastasis of the tinnor cells was determined by counting the minor nodules in the liver on the fourteenth clay after injection of the tumor cells. The mean nodule count in the mice that had received the injections of active substance was 30, while the mean nodule count of the mice in the control group was 140. These results indicate that the active substance isolated from S. pyogenes in accordance with the present invention clearly has a restrictive effect on tumor metastasis.

Industrial Applicability

The biologically active substance from S. pyogenes of the present invention will find primary applicability in conditions in which the proliferation of lymphocytes is desirable, to provide protection against bacterial and vital infection and to restrict tumor metastasis.

We claim:

1. A stable biologically active protein having a molecular weight of 20,000 to 30,000 and an isoelectric point of 8.0 to 10.0 with the amino acid composition:

| Aspartic acid | 3.2 nm % |
|---|---|
| Threonine | 7.5 |
| Serine | 2.9 |
| Glutamic acid | 19.5 |
| Proline | 1.9 |
| Glycine | 30.0 |
| Alanine | 2.3 |

| Valine | 4.7 |
|---|---|
| Methionine | 3.6 |
| Isoleucine | 1.3 |
| Leucine | 11.5 |
| Tyrosine | 0.3 |
| Phenylalanine | 2.0 |
| Lysine | 2.2 |
| Histidine | 5.2 |
| Arginine | 1.9 | obtained from a culture of Streptococcus pyogenes.

2. A method of producing the stable biologically active protein of claim 1, wherein said protein is collected from culture fluid of said culture of Streptoccus pyogenes, concentrated and purified by ion-exchange chromatography, filtration and freeze-drying.

3. The stable biologically active protein of claim 5, wherein said stable, biologically active protein is obtained from a culture of a strain of Streptococcus pyogenes selected from the group consisting of Streptococcus pyogenes Su, Streptococcus pyogenes Sv, Streptococcus pyogenes T-12 and Streptococcus pyogenes C-203.

4. A method of purifying the stable biologically active protein of claim 1, including the steps of:

(a) obtaining culture fluid from a culture of Streptococcus pyogenes in a liquid culture medium;

(b) adding ammonium sulfate to said culture fluid to 60% saturation at 4° C. to form a mixture and letting the mixture stand for 1 hour to form a precipitate;

(c) collecting the precipitate by centrifugation at 8,000×G for 30 minutes;

(d) dialyzing the precipitate into 20 mM acetate buffer at pH 5.0;

(e) passing the dialyzed precipitate and 0.1M acetate buffer through a CM-cellulose column equilibrated with 0.1M acetate buffer and collecting and disposing of the fraction passing through the column;

(f) eluting and collecting an active fraction with 0.5M acetate buffer and dialyzing and freeze-drying the collected active fraction;

(g) passing the freeze-dried active fraction and 20 mM Tris-HCl buffer through a Sephacryl S-200 column equilibrated with 20 mM Tris-HCl buffer at at 7.4 and collecting a fraction with a molecular weight of 20,000 to 30,000;

(h) passing the fraction collected in (g) and 20 mM Tris-HCl buffer through a Sephadex G-50 column, discarding an initial flow-through fraction, collecting the molecular weight 20,000 to 30,000 fraction and freeze-drying said molecular weight 20,000 to 30,000 fraction; and (i) purifying the freeze-dried fraction produced in (h) by passage through a Sephadcx G-50 column with 20 mM Tris-HCl buffer to produce said biologically active protein.

* * * * *